(12) United States Patent
Barker et al.

(10) Patent No.: US 11,643,381 B2
(45) Date of Patent: May 9, 2023

(54) PROCESSES FOR ALDEHYDE SYNTHESIS

(71) Applicant: Hexion Inc., Columbus, OH (US)

(72) Inventors: James M. Barker, Baton Rouge, LA (US); Roy Smith, Diboll, TX (US); Gerlof Bouma, Rotterdam (NL)

(73) Assignee: HEXION INC., Columbus, OH (US)

( * ) Notice: Subject to any disclaimer, the term of this patent is extended or adjusted under 35 U.S.C. 154(b) by 0 days.

(21) Appl. No.: 17/846,861

(22) Filed: Jun. 22, 2022

(65) Prior Publication Data

US 2023/0009838 A1 Jan. 12, 2023

Related U.S. Application Data

(60) Provisional application No. 63/219,553, filed on Jul. 8, 2021.

(51) Int. Cl.
*C07C 45/38* (2006.01)

(52) U.S. Cl.
CPC ................... *C07C 45/38* (2013.01)

(58) Field of Classification Search
CPC ..................................... C07C 45/38
See application file for complete search history.

(56) References Cited

U.S. PATENT DOCUMENTS

| | | | | |
|---|---|---|---|---|
| 4,816,606 A | * | 3/1989 | Brenner | ................. C07C 45/39 568/360 |
| 6,613,949 B1 | | 9/2003 | Wagner | |
| 8,865,943 B2 | * | 10/2014 | Menne | ................... C07B 41/06 568/902.2 |
| 2002/0183559 A1 | | 12/2002 | Carter | |
| 2004/0044252 A1 | | 3/2004 | Liu et al. | |
| 2010/0267993 A1 | | 10/2010 | Deshmukh et al. | |
| 2017/0297989 A1 | | 10/2017 | Araya Brenes | |
| 2018/0148399 A1 | | 5/2018 | Holmberg | |
| 2018/0362453 A1 | | 12/2018 | Erlandsson et al. | |
| 2020/0009535 A1 | * | 1/2020 | Troussard | ................ B01J 35/04 |

OTHER PUBLICATIONS

Helmenstine, Anne Marie, Ph.D. "The Chemical Composition of Air." ThoughtCo, Apr. 4, 2022, thoughtco.com/chemical-composition-of-air-604288.

* cited by examiner

*Primary Examiner* — Sikarl A Witherspoon

(57) ABSTRACT

Methods for aldehyde synthesis are provided. In one embodiment, a method for manufacturing aldehydes includes providing an aldehyde precursor stream and an air stream comprising nitrogen gas and oxygen gas to a reactor comprising a catalyst, reacting the aldehyde precursor stream and the oxygen gas, and converting the air stream to an oxygen gas stream when reacting the aldehyde precursor stream and oxygen gas.

16 Claims, 1 Drawing Sheet

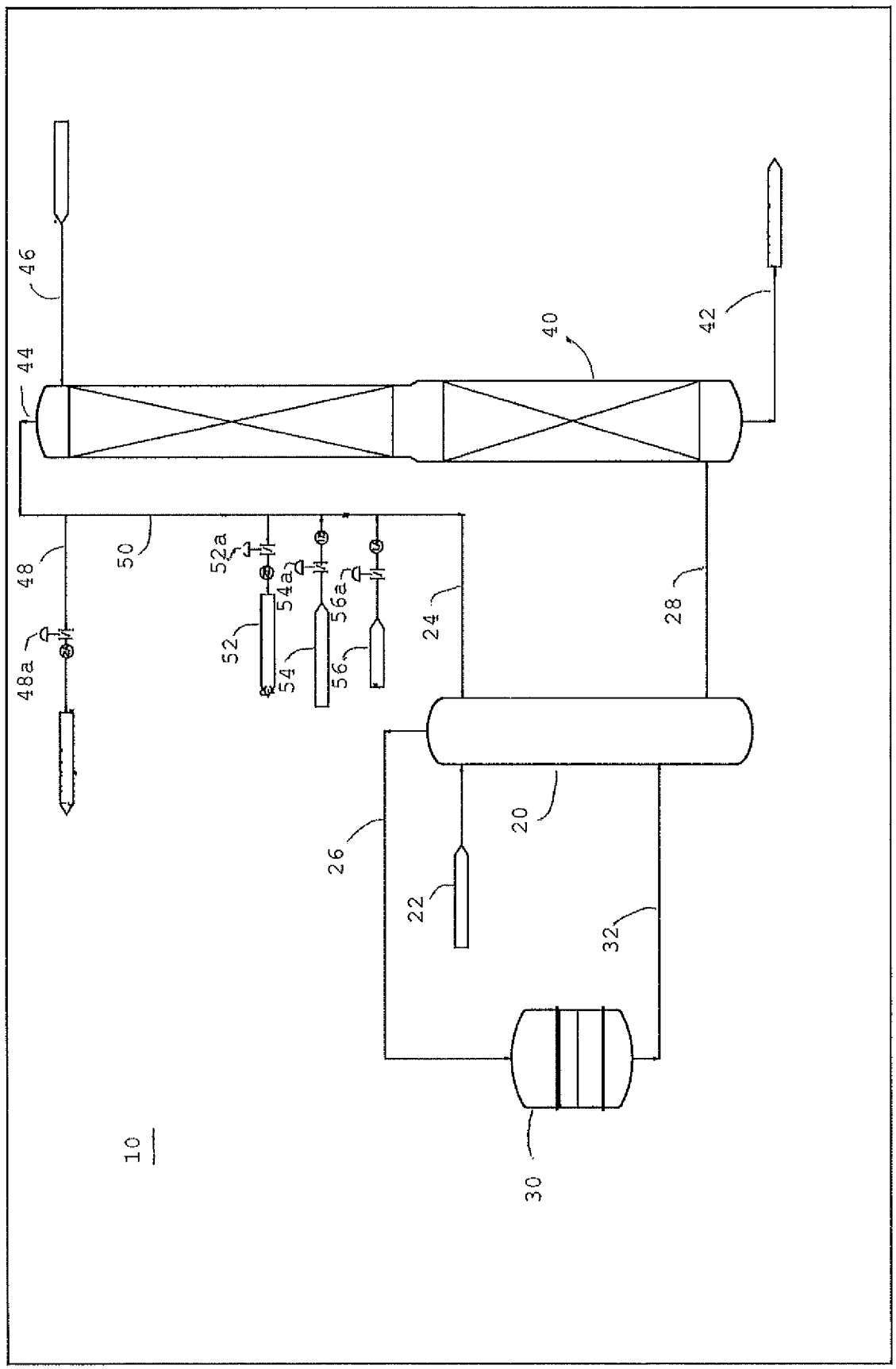

PROCESSES FOR ALDEHYDE SYNTHESIS

RELATED APPLICATION DATA

This application claims benefit to U.S. Provisional Application No. 63/219,553, filed Jul. 8, 2021, of which the entire contents of the application are incorporated by reference herein.

FIELD OF THE INVENTION

The present invention relates to chemical manufacturing processes, in particular, to processes for aldehyde synthesis.

BACKGROUND OF THE INVENTION

Aldehydes are important components used to produce resins, adhesives, plywood and particleboard, insulation, and lubricants. One commonly used process for manufacturing an aldehyde is the catalytic oxygenation of a precursor material. Unfortunately, the catalytic oxygenation of a precursor material often results in high carbon dioxide emissions from the manufacturing plant.

In light of the above, there is a need in the art for aldehyde manufacturing processes that have lower carbon dioxide emissions from the manufacturing plant when compared to the prior art resin manufacturing processes.

SUMMARY OF THE INVENTION

In one aspect, the invention includes a method for manufacturing aldehydes including providing an aldehyde precursor stream and an air stream comprising nitrogen gas and oxygen gas to a reactor comprising a catalyst, reacting the aldehyde precursor stream and the oxygen gas in the reactor, and converting the air stream to an oxygen gas stream comprising oxygen gas when reacting the aldehyde precursor stream and the oxygen gas. In a further embodiment, the air stream has a first oxygen gas concentration, and the oxygen gas stream has a second oxygen gas concentration greater than the first oxygen gas concentration.

In another embodiment, a method is provided for manufacturing aldehydes including providing an aldehyde precursor stream and an air stream to a reactor comprising a catalyst, producing aldehyde and a first post-reaction gas stream comprising nitrogen gas, carbon monoxide, carbon dioxide, and organic compounds, recycling a first portion of the first post-reaction gas stream to the reactor, providing an oxygen gas stream to the reactor with the first post-reaction gas stream, eliminating the air stream to the reactor, and producing aldehyde and a second post-reaction gas stream comprising carbon monoxide and organic compounds.

In another embodiment, a method is provided for manufacturing aldehydes including providing an aldehyde precursor stream and an air stream to a reactor comprising a catalyst, producing aldehyde and a first post-reaction gas stream comprising nitrogen gas, carbon monoxide, and organic compounds, recycling a first portion of the first post-reaction gas stream to the reactor, converting the air stream to an oxygen gas stream, producing aldehyde and a second post-reaction gas stream free of nitrogen gas, and recycling a first portion of the second post-reaction gas stream to the reactor.

DESCRIPTION OF THE FIGURES

The following is a brief description of FIGURES wherein like numbering indicates like elements.

FIG. 1 is a schematic drawing of an exemplary aldehyde manufacturing unit.

DETAILED DESCRIPTION OF THE INVENTION

In one aspect, the invention includes a method for manufacturing aldehydes including providing an aldehyde precursor stream and an air stream comprising nitrogen gas and oxygen gas to a reactor comprising a catalyst, reacting the aldehyde precursor stream and the oxygen gas, and converting the air stream to an oxygen gas stream when reacting the aldehyde precursor stream and the oxygen gas. In a further embodiment, the air stream has a first oxygen gas concentration, and the oxygen gas stream has a second oxygen gas concentration greater than the first oxygen gas concentration.

In comparison with prior art systems, the present invention is to replace air as the oxygen gas ($O_2$) source, which is scientifically accepted as about 21 vol. % oxygen gas, with a high concentration oxygen gas ($O_2$) source, such as from about 90 vol. % oxygen gas to 100 vol. % oxygen gas (pure $O_2$ gas). It is believed that the net effect of this change would be to eliminate the nitrogen gas ($N_2$) brought in with the fresh air thereby replacing the nitrogen gas in a post-reaction gas stream after aldehyde removal, which is referred to as a tail gas, with byproducts of the aldehyde reaction resulting in a higher concentration of byproducts. It is believed that replacing air with $O_2$ will concentrate the carbon monoxide (CO) in the tail gas to about 70 vol. % to about 75 vol %. The tail gas can then be recycled to the reactor, and the CO concentration in the recycle gas to the reactors will increase to the same concentration as $N_2$ is eliminated, effectively replacing the $N_2$. As CO and $N_2$ have similar heat capacities, from a heat balance perspective no significant differences on reactor performance is anticipated.

For portions of the tail gas not recycled, CO is a reactive common chemical building block. A tail gas stream with a high concentration of CO can be either sold to a nearby industrial user or consumed onsite to produce methanol. For example, methanol is the primary raw material needed to manufacture formaldehyde. The end result is beneficial recycling and reuse of the carbon in the tail gas which would otherwise be converted to $CO_2$ and emitted to the atmosphere.

While the invention discloses a process for formaldehyde for illustrative reasons, the invention contemplates this process to be useful for all similar manufacturing processes, such as oxidizing manufacturing processes.

An aldehyde may be manufactured, or synthesized, in a reactor over a catalyst via partial oxidation using air as the oxygen source for oxygen gas.

Suitable catalysts include a material selected from the group consisting of molybdenum, molybdenum oxide, vanadium, vanadium oxide, iron oxide, silver, and combinations thereof. Preferably, a mixed oxide (MO) catalyst including molybdenum and iron oxide may be used. There are several commercial producers of MO catalyst.

An aldehyde precursor is provided to the reactor through an aldehyde precursor stream. The aldehyde precursor stream may comprise methanol, ethanol, and combinations thereof. The aldehyde may be formaldehyde, acetaldehyde, or combinations thereof. In one embodiment, the aldehyde precursor in methanol, and the aldehyde is formaldehyde.

Air is provided to the reactor through the air stream. Air as referenced herein is the scientifically understood atmospheric ambient air. In particular, the scientific acceptance of atmospheric ambient air by volume, dry air contains 78.09% nitrogen gas, 20.95% oxygen gas, 0.93% argon gas, 0.04% carbon dioxide, and small amounts of other gases. Air may also contain a variable amount of water vapor, on average around 1% at sea level, and 0.4% over the entire atmosphere. However, various amounts of components may differ based on local conditions or manufacturing conditions from which air is obtained. For the present invention, air is defined herein as dry air having an oxygen gas ($O_2$) concentration of 23 vol % or less.

In one embodiment, the air stream comprises an oxygen gas concentration from about 19 vol. % to 23 vol. % and a nitrogen concentration from 77 vol. % to about 81 vol. %.

The oxygen gas stream comprises an oxygen gas concentration from greater than 23 vol. % to about 100 vol. %, such as from about 60 vol. % to about 100 vol. %, such as from about 99 vol. % to about 100 vol. %, for example about 99.5 vol. % or 100 vol %. The oxygen gas stream may also comprise a nitrogen concentration less than 77 vol. % to 0 vol. %, such as from about 40 vol. % to 0 vol. %, such as from about 1 vol. % to 0 vol. %, for example about 0.5 vol. % or 0 vol %. In one embodiment, the oxygen gas stream is free of nitrogen gas.

In one embodiment, the oxygen gas stream comprises an oxygen gas concentration from about 90 vol. % to 100 vol. % and a nitrogen concentration from about 10 vol. % to 0 vol. %.

In one embodiment, the air stream has a first oxygen gas concentration, and the oxygen gas stream has a second oxygen gas concentration greater than the first oxygen gas concentration. For example, the air stream may have a first oxygen gas concentration of about 21 vol. %, and the oxygen gas stream has a second oxygen gas concentration of about 99.5 vol % or 100 vol. %.

The oxygen stream and the air stream may be processed though the same equipment and/or gas line, with the oxygen gas stream replacing the air stream.

The process is generally directed to manufacturing aldehydes including providing an aldehyde precursor stream and an air stream comprising nitrogen gas and oxygen gas to a reactor comprising a catalyst, reacting the aldehyde precursor stream and the oxygen gas, and converting the air stream to an oxygen gas stream when reacting the aldehyde precursor stream and the oxygen gas.

In an exemplary operation, the manufacturing unit, such as shown in FIG. 1, would be initially started using fresh air. The use of fresh air at start-up will allow for establishing and stabilizing reaction temperatures that can be controlled during and after the change to an oxygen gas stream. During the stabilizing phase of the start-up, tail gas from the reactor would be directed to a catalytic oxidizer for conversion of all carbon monoxide and trace organics to carbon dioxide.

Once the unit is stable running with fresh air, the controlled conversion (switch over) from air to an oxygen stream, such as about 99.5 vol. % oxygen gas would begin. Oxygen gas is slowly be introduced into the system while at the same time fresh air supply is reduced. The oxygen gas concentration at the reactor inlet is maintained constant during the conversion to control reaction temperatures. Once all of the air has been replaced with oxygen gas, the nitrogen gas formerly present in the recycle and tail gas would be replaced with carbon monoxide and other reaction byproducts. The concentration of carbon monoxide in the recycle and tail gas may be about 75 vol %. The tail gas stream is then suitable for conversion to other products requiring carbon monoxide as a raw material. The general principles and benefits of this would apply to using oxygen gas, or a concentrated stream containing a high concentration of oxygen gas.

In one embodiment of converting the air stream to an oxygen gas stream, the input of an air stream would be closed a certain percentage, such as by a control valve and thereby reducing the supplied amount of air; and the input of an oxygen gas stream would be opened a certain percentage, such as by a control valve and thereby increasing the supplied amount of oxygen gas. The oxygen gas concentration would be monitored to ensure it doesn't drop below a minimum setpoint. The relative closing and opening of the respective steam inputs would proceed in a stepwise process or other process such as a continuous process depending on the controls over the respective inputs, until the air stream has been closed and the oxygen gas concentration is controlled in the proper range. In some embodiment, when the control valve to the oxygen gas stream is opened it will be necessary to gradually close off (or alternatively open) the control valve to any tail gas oxidizer, to maintain the proper recycle gas flow.

Apparatus

An exemplary aldehyde manufacturing process design with chemical unit operations used include reactors, vaporizers, absorber towers, is as follows. The chemical unit may also include among other equipment, such as heat exchangers, which are not detailed herein.

Referring to FIG. 1, an exemplary chemical unit 10 for performing the invention includes a vaporizer 20, reactor 30, and absorber 40.

The vaporizer 20 vaporizes an aldehyde precursor, such as methanol for formaldehyde manufacturing, from an aldehyde precursor stream 22 with an oxygen source from an oxygen source line 24, such as air or purified oxygen gas. Once vaporized, the aldehyde precursor and oxygen source exit the vaporizer 20 to the reactor 30 via vaporizer outlet line 26.

The aldehyde precursor is reacted with the oxygen source in the reactor 30. The reactor may operate at a temperature between 250° C. and 400° C. at atmospheric or above atmospheric pressures. For a formaldehyde reaction, methanol and air are conventionally reacted in the reactor 30. For a formaldehyde reaction according to the present invention, methanol and oxygen gas are conventionally reacted in the reactor 30. For some embodiments of the conversion or transition of air to oxygen gas of a formaldehyde reaction methanol, oxygen gas in the air, and oxygen gas from the oxygen gas line are conventionally reacted in the reactor 30. Following reaction, the post reaction products (post-reaction gas stream) are transported to the absorber 40 via reactor outlet line 32.

In the absorber 40, the aldehyde product is separated from the other reaction products. The aldehyde, such as formaldehyde, is removed from the absorber 40 through the aldehyde product line 42. The remaining reaction products which can include carbon monoxide, carbon dioxide, aldehyde precursor, and organic reaction by-products, such as dimethyl ether and formic acid byproducts, exit the absorber through recycle line 44. The post-reaction gas stream after aldehyde removal is referred to as a tail gas comprises the exiting material. To help in the separation process and exiting of various material from the absorber 40, water may be added from water line 46.

A portion or all of the tail gas in the recycle line may be recycled to the vaporizer 20 for the reactor 30 via line 50 or may be sent to a catalytic converter (not shown), or oxidizer, via line 48 where the tail gas is oxidized to carbon dioxide before emission. In one embodiment, the tail gas may be recycled to the reactor 30 via the vaporizer 20 to dilute the reactants at the reactor inlet, as well as absorb reaction heat. In one embodiment, recycling a portion of the post-reaction gas stream (tail gas) comprises recycling from about 62 vol. % to about 75 vol. %, such as about 70 vol. %, of the post-reaction gas stream, with the remainder transferred to the catalytic converter.

In one embodiment, the tail gas formed from the process using air (about 21% oxygen gas and about 79 vol. % nitrogen gas) which is recycled or converted to carbon dioxide may have a very low concentration of carbon dioxide precursors, such as about 1 vol. % to about 2 vol % carbon monoxide and less than 1 vol % of organic compounds including precursors and reaction by-products with the majority component of tail gas is about 86 vol. % to about 89 vol % nitrogen gas ($N_2$) when the reaction uses air. Carbon dioxide up to 1 vol. %, oxygen gas up to 6 vol. %, and/or water vapor up to 6 vol. % may also be present in the tail gas. In one embodiment, the less than 1 vol % of organic compounds includes less than 1 vol. % dimethyl ether, less than 1 vol. % aldehyde, and/or less than 1 vol. % aldehyde precursor, such as methanol for formaldehyde synthesis.

In an embodiment using oxygen gas, the tail gas is believed to be about 70 vol. % to about 75 vol. % carbon monoxide, about 15 vol. % to about 17 vol. % dimethyl ether, less than 1 vol. % of organic compounds including precursors and reaction by-products, and if present, less than 1 vol. % of nitrogen gas (and argon gas). Carbon dioxide up to 1 vol. %, oxygen gas up to 6 vol. %, and/or water vapor up to 4 vol. % may also be present in the tail gas. In one embodiment, the less than 1 vol % of organic compounds includes less than 1 vol. % aldehyde and/or less than 1 vol. % of aldehyde precursor, such as methanol for formaldehyde synthesis.

Line 50 from the absorber to the vaporizer becomes the reactor's oxygen source line 24, after addition of an oxygen source via air stream 56 or oxygen gas stream 54. Concentrated carbon monoxide gas in line 50 may be drawn off using control valve 52 via line 52, which is upstream of the oxygen inputs of the air stream 56 or the oxygen gas stream 54. Alternatively, stream 52 could be shown coming off stream 48. Stream 48 is directed to an oxidizer (not shown). Stream 52 may be directed to a nearby industrial user or consumed onsite for chemical synthesis.

In an example of converting (or transitioning) the air stream to an oxygen gas stream, the unit 10 is first started up using air stream 56 at minimum design rates. The air will typically be 21 vol. % oxygen gas and 79 vol. % nitrogen gas, however, local conditions may vary. The conversion or transition begins by closing the air control valve 56a of the air stream 56 in about 5% increments while the control valve 54a on the oxygen gas stream 54 is opened in about 1% increments. During the transition, the control valve 48a to the tail gas oxidizer by stream 48 is controlled to monitor and maintain the oxygen gas concentration at the reactor inlet at or below 11.5 vol. % (to avoid deflagration), and the reactor outlet monitored and maintained at or above 4.0 vol. % (to prevent irreversible catalyst damage). The valve operation described above would continue until the air control valve 56 is fully closed with the oxygen gas concentration in the reactor inlet and outlet controlled in the proper range.

In one example of the exemplary process, before conversion or transition, the input is about 21 vol. % oxygen gas and about 79 vol. % nitrogen gas ($N_2$), and the tail gas is believed to be about 86 vol. % to 89 vol. % nitrogen gas ($N_2$), about 1 vol. % to about 2 vol. % carbon monoxide, about 5 vol. % to about 6 vol. % oxygen gas, about 5 vol. % to about 6 vol. % water, less than 1 vol. % carbon dioxide, less than 1 vol. % dimethyl ether, less than 1 vol. % aldehyde, such as formaldehyde, and less than 1 vol. % aldehyde precursor, such as methanol for formaldehyde synthesis.

After conversion or transition, the input is believed to be 99+ vol. % oxygen gas ($O_2$) and less than 1 vol. % nitrogen gas ($N_2$) an argon gas, and the tail gas is believed to be about 70 vol. % to about 75 vol. % carbon monoxide, about 15 vol. % to about 17 vol. % dimethyl ether, about 5 vol. % to about 6 vol. % oxygen gas, about 3 vol. % to about 4 vol. % water, about 0.5 vol. % to about 1 vol. % carbon dioxide, less than 1 vol. % aldehyde, such as formaldehyde, and less than 1 vol. % aldehyde precursor, such as methanol for formaldehyde synthesis.

While the present invention has been described and illustrated by reference to particular embodiments, those of ordinary skill in the art will appreciate that the invention lends itself to variations not necessarily illustrated herein.

What is claimed is:

1. A method for manufacturing aldehydes, comprising:
providing an aldehyde precursor stream and an air stream comprising an oxygen gas in a first concentration from about 19 vol. % to 23 vol. % and a nitrogen in a first concentration from 77 vol. % to about 81 vol. % to a reactor comprising a catalyst;
reacting the aldehyde precursor stream and the oxygen gas in the first concentration in the reactor; and
converting the air stream to an oxygen gas stream comprising an oxygen gas in a second concentration from about 90 vol. % to 100 vol. % and a second nitrogen concentration from about 10 vol. % to 0 vol. % when reacting the aldehyde precursor stream and the oxygen gas in the second concentration.

2. The method of claim 1, wherein the aldehyde precursor stream comprises methanol, ethanol, and combinations thereof.

3. The method of claim 1, wherein the catalyst is a material selected from the group consisting of molybdenum, molybdenum oxide, vanadium, vanadium oxide, iron oxide, silver, and combinations thereof.

4. The method of claim 3, wherein the catalyst comprises molybdenum and iron oxide.

5. The method of claim 1, wherein the air stream comprises an oxygen gas at a concentration of about 21 vol. %.

6. The method of claim 1, wherein the oxygen gas stream comprises an oxygen gas at a concentration of about 99.5 vol. %.

7. A method for manufacturing aldehydes, comprising:
providing an aldehyde precursor stream and an air stream comprising an oxygen gas in a first concentration from about 19 vol. % to 23 vol. % and a nitrogen in a first concentration from 77 vol. % to about 81 vol. % to a reactor comprising a molybdenum and iron oxide catalyst;
producing an aldehyde and a first post-reaction gas stream comprising nitrogen gas, carbon monoxide, carbon dioxide, and organic compounds;
recycling, a first portion of the first post-reaction gas stream to the reactor;
providing an oxygen gas stream comprising an oxygen gas in a concentration from about 90 vol. % to 100 vol. % and a second nitrogen concentration from about 10 vol. % to 0 vol. % to the reactor with the first post-reaction gas stream;

eliminating the air stream to the reactor; and
producing aldehyde and a second post-reaction gas stream comprising carbon monoxide and organic compounds.

8. The method of claim 7, wherein the aldehyde precursor stream comprises methanol, ethanol, and combinations thereof.

9. The method of claim 7, wherein the air stream comprises an oxygen gas concentration of about 21 vol. %.

10. The method of claim 7, wherein the oxygen gas stream comprises an oxygen gas concentration of about 99.5 vol. %.

11. The method of claim 7, further comprising oxidizing a second portion of the post-reaction gas stream to carbon dioxide.

12. The method of claim 7, wherein the recycling the first portion of the first post-reaction gas stream comprises recycling from about 62 vol. % to about 75 vol. %.

13. The method of claim 7, wherein the second post-reaction gas stream is free of nitrogen gas.

14. The method of claim 7, wherein the organic compounds comprise dimethyl ether and formic acid byproducts.

15. The method of claim 7, wherein the aldehyde comprises formaldehyde.

16. A method for manufacturing aldehydes, comprising:

providing an aldehyde precursor stream and an air stream comprising an oxygen gas in a first concentration from about 19 vol. % to 23 vol % and a nitrogen in a first concentration from 77 vol. % to about 81 vol. % to a reactor comprising a catalyst;

producing an aldehyde and a first post-reaction gas stream comprising nitrogen gas, carbon monoxide, and organic compounds;

recycling a first portion of the first post-reaction gas stream to the reactor;

converting the air stream to an oxygen gas stream comprising an oxygen gas in a second concentration from about 90 vol. % to 100 vol. % and a second nitrogen concentration from about 10 vol. % to 0 vol. %;

producing aldehyde and a second post-reaction gas stream free of nitrogen gas; and recycling a first portion of the second post-reaction gas stream to the reactor.

* * * * *